US011857619B2

(12) United States Patent
Rode et al.

(10) Patent No.: US 11,857,619 B2
(45) Date of Patent: Jan. 2, 2024

(54) MULTIMODAL CHROMATOGRAPHY METHOD FOR THE PURIFICATION OF HIV-1 ENVELOPE GLYCOPROTEIN

(71) Applicant: Janssen Vaccines & Prevention B.V., Leiden (NL)

(72) Inventors: Christopher Rode, Downingtown, PA (US); Brian Polilli, Phoenixville, PA (US); John Schreffler, Downingtown, PA (US)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 17/091,296

(22) Filed: Nov. 6, 2020

(65) Prior Publication Data

US 2021/0138060 A1 May 13, 2021

Related U.S. Application Data

(60) Provisional application No. 63/105,664, filed on Oct. 26, 2020, provisional application No. 62/932,180, filed on Nov. 7, 2019.

(51) Int. Cl.
| | |
|---|---|
| *A61K 39/21* | (2006.01) |
| *C07K 14/16* | (2006.01) |
| *C12N 7/02* | (2006.01) |
| *C07K 1/18* | (2006.01) |
| *C07K 14/005* | (2006.01) |
| *A61K 39/00* | (2006.01) |

(52) U.S. Cl.
CPC ............... *A61K 39/21* (2013.01); *C07K 1/18* (2013.01); *C07K 14/005* (2013.01); *C07K 14/162* (2013.01); *C12N 7/02* (2013.01); *A61K 2039/53* (2013.01); *C12N 2740/16051* (2013.01); *C12N 2740/16111* (2013.01); *C12N 2740/16122* (2013.01); *C12N 2740/16134* (2013.01)

(58) Field of Classification Search
CPC .............. A61K 39/21; C07K 14/162; C12N 2740/16111; C12N 2740/16051
See application file for complete search history.

(56) References Cited

U.S. PATENT DOCUMENTS

| | | | | |
|---|---|---|---|---|
| 10,137,191 | B2 * | 11/2018 | Barouch | ............... C07K 14/005 |
| 10,144,774 | B2 * | 12/2018 | El Menyawi | ........ C07K 16/065 |
| 10,526,583 | B2 * | 1/2020 | Potter | ...................... C12N 7/00 |
| 2010/0297604 | A1 * | 11/2010 | Li | ..................... G01N 33/56983 435/5 |

FOREIGN PATENT DOCUMENTS

| | | | |
|---|---|---|---|
| WO | 2007149490 | A1 | 12/2007 |
| WO | 2010042942 | A2 | 4/2010 |
| WO | 2011110598 | A1 | 9/2011 |
| WO | 2014107744 | A1 | 7/2014 |
| WO | 2016049287 | A1 | 3/2016 |
| WO | 2016073401 | A1 | 5/2016 |
| WO | 2017102929 | A1 | 6/2017 |
| WO | 2017192434 | A1 | 11/2017 |
| WO | 2017216288 | A1 | 12/2017 |
| WO | 2019016062 | A1 | 1/2019 |
| WO | 2020117760 | A1 | 6/2020 |

OTHER PUBLICATIONS

Zhang, K., and X. Liu, 2016, Mixed-mode chromatography in pharmaceutical and biopharmaceutical applications, J. Pharm. Biomed. Analysis 128:73-88.*
Pinto, I. F., et al., 2015, Multimodal chromatography: debottlenecking the downstream processing of monclonal antibodies, Pharm. Bioprocess. 3(3):263-279.*
Zhao, G., et al., 2009, Ligands for mixed-mode protein chromatography: Principles, characteristics and design, J. Biotechnology 144:3-11.*
Halan, V., et al., 2019, Multimodal chromatography for purificatio of biotherapeutics—A review, Curr. Prot. Peptide Sci. 20:4-13.*
Berman, P. W., et al., Aug. 1989, Expression and immunogenicity of the extracellular domain of the human immunodeficiency virus type 1 envelope glycoprotein, gp160, J. Virol. 63(8):3489-3498.*
International Search Report dated May 19, 2021 in PCT/EP2020/081271.
Written Opinion dated May 19, 2021 in PCT/EP2020/081271.
J.P. Nkolola, et al., "Characterization and Immunogenicity of a Novel Mosaic M HIV-1 gp140 Trimer," Journal of Virology, vol. 88, No. 17, pp. 9538-9552, Sep. 1, 2014.
Srivastava Indresh K., et al., "Purification and characterization of oligomeric envelop glycoprotein from a primary R5 subtype B human immunodeficiency virus," Journal of Virology, The American Society For Microbiology, vol. 76, No. 6, pp. 2835-2847, Mar. 1, 2002.
Martin, G., et al., "A simple one-step method for the preparation of HIV-1 envelope glycoprotein immunogens based on a CD4 mimic peptide," Virology, Elsevier, Amsterdam, NL, vol. 381, No. 2, pp. 241-250, Nov. 25, 2008. Abhinav A. Shukla, et al., "A vaccine Approach against HIV-1, Manufacturing Env proteins: from Bench to Bedside," Health & Medicine, Slideshare, pp. 1-32, Nov. 2, 2016.
Anonymous: "The use of Capto Core 700 and Capto Q ImpRes in the purification of Human Papilloma Virus Like Particles," May 18, 2014, Retrieved from the Internet: URL: http://www.processdevelopmentforum.com/files/articles/Purification_of_HPV_VLP_using_Capto(TM)_Core_May19.pdf. Retrieved Jul. 15, 2020.

(Continued)

*Primary Examiner* — Jeffrey S Parkin

(74) *Attorney, Agent, or Firm* — Ice Miller LLP

(57) ABSTRACT

Described herein is a process for protein purification, particularly a process for the purification of a glycoprotein, such as an HIV envelope protein, useful for vaccines or biotherapeutics.

14 Claims, 3 Drawing Sheets

Specification includes a Sequence Listing.

(56) References Cited

OTHER PUBLICATIONS

Halan Vivek, et al., "Multimodal Chromatography for Purification of Biotherapeutics—A Review," Current Protein and Peptide Science, vol. 20, No. 1, pp. 4-13, Nov. 9, 2018.
Barouch Dan H., et al., "Mosaic HIV-1 Vaccines Expand the Breadth and Depth of Cellular Immune Response in Rehesus Monkeys," Nat Med vol. 16, No. 3 pp. 319-323 (2010).
Kovacs, James M., et al., "HIV-1 envelope trimer elicits more potent neutralizing antibody responses than monomeric gp 120," PNAS vol. 109, No. 30, pp. 12111-12116, Jul. 24, 2012.

* cited by examiner

| Stage 1 |
|---|
| Cell Expansion (Preculture) |
| Stage 2 |
| Fed-Batch Production Bioreactor |
| Stage 3 & 4 |
| Low pH Flocculation & Clarification |
| Stage 5 |
| Initial UFDF |
| Stage 6 |
| Capto™ MMC ImpRes Chromatography |
| Stage 7 |
| POROS™ HQ Chromatography |

| Stage 8 |
|---|
| Capto™ DeVirS Chromatography |
| Stage 9 |
| Low pH Viral Inactivation |
| Stage 10 |
| Capto™ Adhere Chromatography |
| Stage 11 |
| Viral Retentive Filtration |
| Stage 12 |
| Ultrafiltration / Dia-filtration |
| Stage 13 |
| Final Formulation |

Fig. 3

| Stage 1 |
|---|
| Cell Expansion (Preculture) |
| Stage 2 |
| Fed-Batch Production Bioreactor |
| Stage 3 |
| Low pH Flocculation |
| Stage 4 |
| Clarification |
| Stage 5 |
| Capto™ MMC ImpRes Chromatography |
| Stage 6 |
| POROS™ HQ Chromatography |

| Stage 7 |
|---|
| Low pH Viral Inactivation |
| Stage 8 |
| Capto™ Adhere Chromatography |
| Stage 9 |
| Viral Retentive Filtration |
| Stage 10 |
| Ultrafiltration/Diafiltration |
| Stage 11 |
| Final Formulation (DS @ 0.59 mg/mL) |

Fig. 4

# MULTIMODAL CHROMATOGRAPHY METHOD FOR THE PURIFICATION OF HIV-1 ENVELOPE GLYCOPROTEIN

CROSS REFERENCE TO RELATED APPLICATION

This application claims priority to U.S. Provisional Application Nos. 62/932,180 filed on Nov. 7, 2019, and 63/105,664 filed on Oct. 26, 2020, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "004852_156US3 Sequence Listing" and a creation date of Jul. 22, 2020 and having a size of 13 kb. The sequence listing submitted via EFS-Web is part of the specification and is herein incorporated by reference in its entirety.

BACKGROUND OF THE INVENTION

Human Immunodeficiency Virus (HIV) affects millions of people worldwide, and the prevention of HIV through an efficacious vaccine remains a very high priority, even in an era of widespread antiretroviral treatment. The high genetic variability of HIV-1 makes the development of a HIV-1 vaccine an unprecedented challenge. In order to improve coverage of potential T-cell epitopes, and improve cellular responses, "mosaic" HIV-1 Gag, Pol and Env antigens, derived from HIV Group Antigen (Gag), polymerase (Pol), and envelope (Env) proteins, were described by others and developed in an attempt to provide maximal coverage of potential T-cell epitopes (e.g., Barouch et al, *Nat Med* 2010, 16: 319-323). The mosaic antigens are similar in length and domain structure to wild-type, naturally occurring HIV-1 antigens.

An efficacious vaccine against HIV may involve one or more immunogenic proteins that are highly glycosylated, e.g., with 20 or more glycosylation sites. Some of the (glycosylated) proteins may also be significantly larger than the standard monoclonal antibodies used in biotherapeutics. There is a need for an improved process for the production and purification of proteins, particularly glycosylated immunogenic proteins, which can be used as an active ingredient in a vaccine or other pharmaceutical compositions. Preferably, the process could improve the yield, maintain the conformation stability of the protein of interest and be easily adaptable into existing facilities for large scale production and/or purification, while having acceptable overall recovery and high purity of the protein.

Different proteins behave differently, and despite many different possible purification methods that have been described for various proteins, it is inherently unpredictable which process will meet the requirements above for a given protein.

BRIEF SUMMARY OF THE INVENTION

The invention relates to a process for the purification of a protein, preferably a glycosylated protein, such as a human immunodeficiency virus (HIV) antigenic protein, more preferably an HIV envelope protein, such as the envelope proteins of HIV-1 clade C or mosaic envelope protein, such as HIV gp140 protein, e.g. trimeric HIV clade C gp140 protein or trimeric HIV mosaic gp140 protein.

In one general aspect, the invention relates to a process of purifying a protein, such as a human immunodeficiency virus (HIV) envelope protein, comprising:
  a. obtaining a cell sample, such as a cell supernatant, comprising the protein;
  b. adjusting the pH of the cell sample, to about 5.0 to thereby precipitate host cell proteins (HCPs) in the cell sample;
  c. removing the precipitated HCPs from the cell sample by depth filtration to obtain a filtrate comprising the protein; and
  d. purifying the protein from the filtrate by chromatography.

In some embodiments, the HIV envelope protein is gp140 of HIV-1 clade C, or gp140 mosaic protein.

In some embodiments, the cell sample, such as cell supernatant, is from host cells that recombinantly express the protein, such as eukaryotic host cells, preferably mammalian host cells. In certain embodiments, the host cells produce the protein in a fed-batch process in a bioreactor. In certain embodiments, the bioreactor has a volume of between about 1 L and about 20000 L, e.g. from about 10 L to about 16500 L.

In certain embodiments, host cells are removed, e.g. by gravity settling, or preferably by centrifugation, more preferably continuous centrifugation, before adjusting the pH of the cell sample, such as cell supernatant.

In certain embodiments, host cells are removed, e.g. by gravity settling, or preferably by centrifugation, more preferably continuous centrifugation, after adjusting the pH of the cell sample by a low pH flocculation.

In certain embodiments, the process further comprises one or more ultrafiltration and diafiltration (UFDF) steps. For example, the depth filtration in step c) can be followed by an ultrafiltration and diafiltration (UFDF) step.

In certain embodiments, the protein is HIV envelope protein, e.g. HIV-1 clade C gp140 or HIV-1 mosaic gp140, and the chromatography includes a capture step using a multimodal resin (also called mixed mode resin), preferably comprising hydrophobic interaction and cation exchange properties. It was surprisingly found that such resins gave good purification results. In certain non-limiting examples, the multimodal resin is Capto MMC or Capto MMC ImpRes (commercially obtainable from Cytiva). In certain embodiments, the HIV envelope protein is loaded at a certain salt concentration and pH, and eluted in purer form at an increased salt concentration and increased pH as compared to the loading conditions.

In certain embodiments, the partially purified HIV envelope protein that has been eluted from the multimodal resin in the capture step is subjected to a second chromatography process step, e.g. an orthogonal chromatography step. In certain preferred embodiments, the second chromatography step comprises an anion exchange resin, such as a weak anion exchange resin (e.g. Capto DEAE), or preferably a strong anion exchange resin (e.g. POROS 50 HQ). Preferably the HIV envelope protein is bound to this resin and subsequently eluted in purer form, e.g. using increased salt concentration for elution as compared to loading conditions.

In certain embodiments, the HIV envelope protein containing fraction is subjected to a $3^{rd}$ chromatography step, using a resin that comprises the ligand dextran sulfate, e.g. Capto DeVirS (a cation medium known to have affinity-like behavior to different types of virus). The HIV envelope protein binds to this resin and can subsequently be eluted in further purified form, e.g. using increased salt concentration as compared to the loading conditions of this resin. This step is particularly useful if the protein is clade C gp140 protein.

In certain embodiments, a low pH viral inactivation step, e.g. holding for about one hour at about pH 3.5 and subsequently filtering through a 0.45-0.2 micrometer filter, is performed after the second chromatography step in case the resin with the ligand dextran sulfate is not used, or after the third chromatography step in case the resin that comprises the ligand dextran sulfate is used.

In certain embodiments, a fourth chromatography step is performed (which is the third chromatography step in cases where the resin that comprises the ligand dextran sulfate as described above is not used, e.g. for mosaic gp140 protein), wherein the HIV envelope containing fraction of the previous chromatography step (either second or third chromatography step as described above) is applied to a mixed mode resin that has anion-exchange and hydrophobic functionalities, e.g. Capto Adhere resin. In certain embodiments of the invention the mixed mode resin in this step is used in bind and elute mode. In other embodiments of the invention this resin is used in flow-through mode. The skilled person is able to choose conditions that are suitable for either mode of use of such resin, as a polishing step for purification of an HIV envelope protein in view of the present disclosure. This chromatography step can further reduce hexamer and host cell protein impurities from the HIV envelope protein, which preferably comprises trimeric HIV-1 gp140.

In certain embodiments, the purified HIV envelope protein from the last chromatography step above is subjected to a viral retentive filtration step, e.g. using a Virosart HC or a Planova 20N filter.

In certain embodiments, the purified HIV envelope protein is subjected to a final UFDF step. The resulting material can be formulated into its final formulation, e.g. for use as a vaccine.

It is an aspect of the invention to provide a process for purifying HIV-1 gp140 protein, comprising capturing the protein on a multimodal resin comprising hydrophobic interaction and cation exchange properties, and eluting a purified fraction from said resin, wherein the purity of the HIV-1 gp140 protein is substantially increased as compared to the protein in the mixture that was loaded on the resin during the capturing step. Such multimodal resins appear particularly suitable for purification of HIV-1 gp140 protein.

In another aspect of the invention, a process for purifying HIV-1 gp140 protein is provided, the process comprising the steps of:
i) providing a composition comprising HIV-1 gp140 protein and other, non-desired proteins, such as host cell proteins derived from the host cell in which HIV-1 gp140 protein was expressed;
ii) capturing the HIV-1 gp140 protein on a multimodal resin comprising hydrophobic interaction and cation exchange properties, and eluting a purified fraction comprising the HIV-1 gp140 protein from said resin;
iii) applying the purified fraction of step ii) to an anion exchange resin to bind the HIV-1 gp140 protein, and eluting a further purified fraction comprising the HIV-1 gp140 protein from said resin;
iv) subjecting the further purified fraction of step iii) to a mixed mode resin that has anion-exchange and hydrophobic functionalities, and eluting a further purified HIV-1 gp140 protein. In preferred embodiments the HIV-1 gp140 protein in this process is mosaic gp140 protein.

In certain embodiments of this process, the process comprises the further step of applying the further purified fraction of HIV-1 gp140 protein of step iii) to a resin that comprises the ligand dextran sulfate, and eluting a further purified fraction comprising the HIV-1 gp140 protein from said resin, before subjecting this fraction to step iv) of this process. These embodiments are particularly useful when the HIV-1 gp140 protein is clade C gp140 protein.

BRIEF DESCRIPTION OF THE SEVERAL VIEWS OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 3 illustrates a process flow chart for the purification of gp140 of HIV-1 clade C; and FIG. 4 illustrates a process flow chart for the purification of gp140 mosaic protein.

DETAILED DESCRIPTION OF THE INVENTION

Figure 1A:
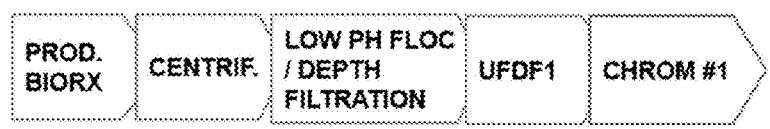
FIG. 1A shows a process for protein purification including centrifugation followed by low pH flocculation and depth filtration, and column chromatography (chrom #1 for HIV-1 gp140 protein can for instance be a capture step using a mixed mode resin comprising hydrophobic interaction and cation exchange properties)

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the term "about," when used in conjunction with a number, refers to any number within ±10%, e.g. ±5%, or ±1%, of the referenced number. For example, a pH of about 5.0 means any pH from 4.5-5.5, inclusive.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to who will be or has been administered a protein or vaccine according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The invention generally relates to a process of purifying a protein, preferably a glycosylated protein, more preferably a human immunodeficiency virus (HIV) envelope protein, such as the envelope protein of HIV-1 clade C or HIV-1 mosaic envelope protein, the process comprises:
 a. obtaining a cell sample, such as a cell supernatant, comprising the protein;
 b. adjusting the pH of the cell sample to about 5.0 to thereby precipitate host cell proteins (HCPs) in the cell sample;
 c. removing the precipitated HCPs from the cell sample by depth filtration to obtain a filtrate comprising the protein; and
 d. purifying the protein in the filtrate by chromatography.

Preferably, the cell sample is a cell supernatant comprising the protein secreted by the cell. The cell sample can also be a cell lysate or a processed cell lysate comprising the protein produced by the cell. Such lysate can for instance be prepared by breaking down of the membrane of a cell. A cell sample useful for a process of the application can be obtained using methods known in the art in view of the present disclosure. For example, a cell supernatant can be obtained by applying a cell culture to centrifugation to remove cells. A cell lysate can be obtained by disrupting or lysing the cells and removing the cell debris by centrifugation. The cell supernatant or cell lysate can be used directly or it can be further processed before being used for a process of the application. Preferably, a continuous centrifugation is used to remove cells produced from a bioreactor to obtain a cell sample useful for a process of the application.

In some embodiments, the host cells produce the protein in a fed-batch process in a bioreactor.

In certain embodiments, the bioreactor has a volume of between about 1 L and about 20000 L, e.g. from about 10 L to about 16500 L, e.g. from about 100 L to about 15000 L.

The pH of the cell sample, such as a cell supernatant, can be adjusted, for example, by adding a suitable amount of acid (e.g., 1M acetic acid) to the cell sample to precipitate host cell proteins (HCPs) in the cell sample. This process is sometimes also referred to as "low pH flocculation." Preferably, the pH of the cell sample is adjusted to about 5, e.g., about 4.5, 4.6, 4.7, 4.8, 4.9, 5.0, 5.1, 5.2, 5.3, 5.4, 5.5, or any value in between, to precipitate host cell proteins (HCPs) in the cell sample, while a sufficient amount of the protein of interest (e.g., HIV gp140) in the cell sample is not precipitated. Other proteins in the cell sample, such as proteins in the culture medium for the cells, can also be precipitated at the pH of about 5.

In some embodiments, during the process of low pH flocculation, the cell sample is incubated at about pH 5 for about 15 minutes to about 15 hours, e.g. for about 0.5-12 hours, e.g. about 1-3 hours, e.g. about 3 hours, preferably about 1 hour, to precipitate the HCPs.

In some embodiments, the low pH flocculation can be performed after centrifugation. In preferred embodiments, the low pH flocculation is performed before centrifugation.

The precipitated HCPs from the cell sample can be removed by depth filtration to obtain a filtrate comprising the protein. Depth filters with various media types (single layer or multiple layers of cellulose, polyacrylic fiber, diatomaceous earth, silica, activated carbon, etc.) and various grades can be used for depth filtration in a process of the application in view of the disclosure herein. Examples of the depth filters useful for the invention include, but are not limited to, depth filters available from commercial sources, such as the Millistak+® family and Clarisolve® depth filters from Millipore Sigma. In certain embodiments, the depth filtration uses a depth filter such as a Millistak+® C0HC, C0SP, CE35, CE50, D0HC, D0SP, DE, A1HC, B1HC, F0HC, X0HC, X0SP, etc. Suitable buffers can be used to equilibrate the depth filters prior to use and to chase the filters after the acid precipitated harvest (e.g., precipitated HCPs and other proteins) was filtered through the depth filter. Preferably, the buffer has a pH of about 5.0. Preferably, the depth filtrate is sterile filtered to remove any contaminating microbes, e.g., with a filter pore size of 0.45 µm or less, preferably 0.22 µm.

In certain embodiments, an ultrafiltration and diafiltration (UFDF) step is used to remove HCPs and concentrate the protein of interest (e.g., gp140) prior to or in between of the chromatography steps. Ultrafiltration (UF) is a commonly used process for concentrating a dilute product stream. It separates molecules in solution based on the membrane pore size or molecular weight cutoff. Diafiltration (DF) is often used to exchange product into a desired buffer (e.g., from an elution buffer into a final formulation buffer). UF and DF typically use tangential flow filtration, where feed flows parallel to the membrane surface rather than perpendicular to the surface. Various UF/DF membranes can be used, including, e.g., membranes of cellulose acetate, polyvinylidene fluoride (PVDF), and polyethersulfone (PES). Depending on the need, the membranes used in UF/DF can have different molecular weight cut off (MWCO). For example, the MWCO for a UF/DF can be, e.g., 30, 40, 50, 60, 70, 80, 90, 100, 110, 120, 130, 140, 150 kDa. In some embodiments, the UF/DF is configured with one or more flat plate membranes are stacked together. UF/DF processes include, e.g., sanitization and pre-use testing, equilibration, concentration, diafiltration, product recovery, cleaning and post-use testing, and storage. The integrity of a UF/DF system can be confirmed using a diffusion test. Suitable UF and/or DF buffers can be used for the UF/DF process in view of the present disclosure. For example, the buffer can have a pH of 3.5, 4, 4.5, 5, 5.5, 6, 6.5, 7, 7.5, 8, or 8.5. Various cross-flow rates and membrane load rate can be used depending on the need, in view of the present disclosure.

In some embodiments, a process of the application uses three or more chromatographic column steps. Suitable columns can be used in the invention in view of the present disclosure. Examples of such columns include, but are not limited to, those described in the embodiments, and for instance illustrated in FIGS. 3 and 4.

In one embodiment, a process of the application comprises a capture chromatography step using a multimodal resin (also called mixed mode resin). Multimodal or mixed-mode chromatography resins are based on media that have been functionalized with ligands inherently capable of several different types of interaction: for example combinations of two or more of ion exchange, affinity, size exclusion, and hydrophobic. The ability to merge and take advantage of these modes of protein separations can enhance overall selectivity in a purification process. This enhanced selectivity can be used to remove process impurities in a single column step that would otherwise require multiple processing steps to remove. Preferably, the multimodal resin has hydrophobic interaction and cation exchange properties, which is more salt tolerant, enabling binding of the protein to the resin with minimal or no dilution.

Resins useful for the invention can be in different formats, e.g. as beads, filters (membranes), cartridges, etc., all to be considered as 'resin' according to the invention, and in certain embodiments the resins are in the form of beads that can be used in columns, and that resins that can be used according to the invention can be commercially obtained from vendors, e.g. Cytiva (former GE Healthcare) and/or others. In some embodiment, a multimodal resin can be a resin that is prepared by directly or indirectly immobilizing two or more types of functional groups having different selectivity onto a base resin. For example, a multimodal resin can comprise a multimodal strong anion exchange chromatography material having a matrix of high-flow agarose and a multimodal strong anion exchanger as ligand, or a matrix of high-flow agarose and a multimodal weak cation exchanger as ligand. Specific examples of the multimodal resin can include, but are not limited to, Capto Adhere, Capto MMC, Capto Adhere ImpRes or Capto MMC ImpRes (which are manufactured by Cytiva, Capto is registered trademark), HEA HyperCel, PPA HyperCel, MEP HyperCel (which are manufactured by Pall Corp., HyperCel is trademark), TOYOPEARL (registered trademark) MX-Trp-650M (manufactured by TOSOH Corp.) or the like, but are not limited thereto.

In certain embodiments, the multimodal capture chromatography is performed in the flow-through mode.

In preferred embodiments, the multimodal capture chromatography is performed in the bind and elute mode.

Preferably, the multimodal capture chromatography is performed in the bind and elute mode in order to remove host cell proteins and DNA. The protein of interest is loaded to the multimodal capture resin, e.g. column, at a certain salt concentration and pH and binds to the column, and then is eluted later by an elution solution to obtain a pooled elute. The protein of interest can be loaded to the column in any suitable buffer (such as acetate buffer, histidine buffer, HEPES buffer, phosphate buffer, or Tris buffer) and/or salt solution (such as sodium chloride solution), for instance a solution comprising sodium acetate at about 15-100 mM (e.g., 25 mM) and sodium chloride at about 10-50 mM (e.g., 25 mM), at any suitable pH such as pH between about 4-6 (e.g., pH 4 or 5), and with any suitable conductivity such as conductivity between about 1-50 mS/cm, e.g. e.g. between about 3-50 mS/cm, e.g. between about 5-50 mS/cm, e.g. between about 3-40 mS/cm, e.g. between about 6-40 mS/cm, preferably between about 3-20 mS/cm, e.g. between about 10-20 mS/cm (e.g., about 5 mS/cm, or about 15 mS/cm). The elution solution can comprise any suitable buffer (such as 2-[4-(2-hydroxyethyl)piperazin-1-yl]ethanesulfonic acid (HEPES) buffer) and/or salt solution (such as sodium chloride solution), for instance a solution comprising HEPES at about 20-80 mM (e.g., 50 mM) and sodium chloride at about 50-600 mM, e.g. about 100-600 mM (e.g. 400 mM), and at any suitable pH such as pH between about 4-8, e.g. between about 4.5-7.5 (e.g., pH 7), and with any suitable conductivity such as conductivity between about 10-60 mS/cm (e.g., 40 mS/cm). The protein of interest can also be eluted from the multimodal capture column by gradient elution.

In another embodiment, a process of the application comprises a second chromatography comprising an anion exchange resin. The anion exchanger used in this step can be a strong anion exchanger or a week anion exchanger. Preferably, the anion exchanger comprises an anion exchange ligand such as quaternary ammonium, quaternary aminoethyl, diethylaminoethyl, trimethylaminoethyl, or dimethylaminoethyl. More preferably, the anion exchanger is selected from a weak anion exchange resin (e.g. Capto DEAE) or a strong anion exchange resin (e.g. POROS 50 HQ). Other examples of anion exchanger include, but are not limited to, DEAE Sepharose FF, Q-Sepharose (HP and FF), AEX Sepharose FF (low and high substituted), Capto Q, Q XP, Source 30 Q and 15 Q, most preferably Fractogel DEAE and MPHQ.

In certain embodiments, the second chromatography is performed in the flow-through mode.

In preferred embodiments, the second chromatography is performed in the bind and elute mode.

Preferably, the second chromatography is performed in the bind and elute mode in order to further remove host cell proteins and DNA. The protein of interest is loaded to the anion exchange resin, e.g. column, at a certain salt concentration and pH and binds to the column, and then is eluted later by an elution solution to obtain a pooled elute. The protein of interest can be loaded to the column in any suitable buffer (such as Tris buffer or HEPES buffer) and/or salt solution (such as sodium chloride solution), for instance a solution comprising Tris at about 15-75 mM (e.g., 25 mM), and sodium chloride at about 0-75 mM, e.g. about 25-75 mM (e.g., 50 mM, or e.g. 5 mM), at any suitable pH such as pH between about 6-8 (e.g., pH 7.5 or 8), and with any suitable conductivity such as conductivity between about 2-8 mS/cm (e.g., 5.5 mS/cm). The elution solution can comprise any suitable buffer (such as Tris buffer) and/or salt solution (such as sodium chloride solution), for instance a solution comprising Tris at about 15-75 mM (e.g., 25 mM, or e.g. 50 mM) and sodium chloride at about 50-500 mM, e.g. about 100-300 mM (e.g. 185 mM, or 200 mM), at any suitable pH such as pH between about 6-9 (e.g., pH 7.5), and with any suitable conductivity such as conductivity between about 5-50 mS/cm, e.g. about 5-40 mS/cm (e.g., 20 mS/cm). The protein of interest can also be eluted from the second column by gradient elution.

In another embodiment, a process of the application comprises a third chromatography using an affinity medium that binds to glycan. The affinity medium resin can comprise the ligand sulfate or dextran sulfate. Examples of affinity medium include, but are not limited to, the cellulose sulfate medium or the agarose sulfate medium such as Cellufine sulfate, Cellufine sulfate m, Cellufine sulfate c, Cellulofine sulfate m, Cellulofine sulfate c, Cellufine sulfate m or Cellufine sulfate c (which are manufactured by JNC Corp.), Cytiva CAPTO™ Core 700 or Capto DeVirS (manufactured by Cytiva) or the like.

In certain embodiments, the third chromatography is performed in the flow-through mode.

In preferred embodiments, the third chromatography is performed in the bind and elute mode.

Preferably, the third chromatography is performed in the bind and elute mode in order to further remove host cell proteins and DNA. The protein of interest is loaded to the affinity medium resin, e.g. column, at a certain salt concentration and pH and binds to the column, and then is eluted later by an elution solution to obtain a pooled elute. The protein of interest can be loaded to the column in any suitable buffer (such as Tris buffer or HEPES buffer) and/or salt solution (such as sodium chloride solution), for instance a solution comprising Tris at about 5-25 mM (e.g., 6 mM) or HEPES at about 5-50 mM (e.g., 20 mM), and sodium chloride at about 0-100 mM, e.g. at about 25-75 mM (e.g., 45 mM, or 50 mM), and at any suitable pH such as pH between about 4-8, e.g. between about 5-8 (e.g., pH 6.5), and with any suitable conductivity such as conductivity between about 1-15 mS/cm, e.g. about 1-10 mS/cm (e.g., 5 mS/cm). The elution solution can comprise any suitable buffer (such as Tris buffer) and/or salt solution (such as sodium chloride solution), for instance a solution comprising Tris at about 10-100 mM, e.g. at about 15-75 mM (e.g., 25 mM) and sodium chloride at about 100-300 mM (e.g. 185 mM), and at any suitable pH such as pH between about 6-9 (e.g., pH 7.5), and with any suitable conductivity such as conductivity between about 10-30 mS/cm, e.g. about 15-25 mS/cm (e.g., 19 mS/cm). The protein of interest can also be eluted from the third column by gradient elution.

In certain embodiments, a process of the application comprises a low pH viral inactivation step, e.g. holding for about 15 minutes to about 4 hours, e.g. about one hour at about pH 3-4, e,g. pH about 3.5 and subsequently filtering through a 0.45-0.2 micrometer filter. This step is performed after the second chromatography step in case the third chromatography using an affinity medium is not used, or after the third chromatography step when the third chromatography step is performed. The filtrate is then neutralized to a target pH, such as a pH of 5-7, prior to the next processing step. The low pH viral inactivation step can denature the proteins of virus contaminants, which then can be removed in the subsequent column chromatography.

In another embodiment, a process of the application comprises a fourth chromatography using a multimodal resin, preferably a multimodal resin comprising anion exchange and hydrophobic interaction chromatography functionalities. Specific examples of the multimodal resin can include, but are not limited to, Capto Adhere, Capto MMC, Capto Adhere ImpRes or Capto MMC ImpRes (which are manufactured by Cytiva, Capto is registered trademark), HEA HyperCel, PPA HyperCel, MEP HyperCel (which are manufactured by Pall Corp., HyperCel is trademark), TOYOPEARL (registered trademark) MX-Trp-650M (manufactured by TOSOH Corp.) or the like, but are not limited thereto. A suitable multimodal resin, such as Capto Adhere, can be used in this step in view of the present disclosure. The multimodal chromatography is performed in the bind and elute mode or preferably in flow-through mode. The fourth chromatography can further reduce hexamer and host cell protein impurities in the product pool.

Preferably, the fourth chromatography is performed in the flow-through mode in order to remove host cell proteins and nucleic acids. The protein of interest can be loaded to the resin, e.g. column, in any suitable buffer (such as sodium acetate buffer) and/or salt solution (such as sodium chloride solution), for instance a solution comprising sodium acetate at about 25-75 mM (e.g., 50 mM) and sodium chloride at about 50-800 mM, e.g. about 200-800 mM (e.g., 317 mM or 650 mM), and at any suitable pH such as pH between about 3-8, e.g. between about 3-5 (e.g., pH 3.5 or 4.5), and with any suitable conductivity such as conductivity between about 5-70 mS/cm. Preferably, the flow-through solution comprises the HIV Env protein, e.g. gp140 protein, while certain impurities remain bound to the column.

In yet another embodiment, a process of the application comprises one or more of a nanofiltration (viral retentive filtration) step and a final UFDF step. A viral-retentive filtration operates on a size exclusion principle. For example, a virus filter having an effective pore size of maximum 75 nm can be used for the viral retentive filtration. Examples of the filters for the viral-retentive filtration include, but are not limited to, Virosart HC, Virosart® HF, a Planova 20N filter, etc.

In yet another embodiment, a process of the application comprises a final formulation step, wherein the purified protein can be formulated into a final product, such as a vaccine or an immunogenic composition. Final products of the invention can be formulated in any matter suitable for administration to a subject to facilitate administration and improve efficacy, including, but not limited to, oral (enteral) administration and parenteral injections.

Each of the chromatography steps can be performed under suitable conditions in view of the disclosure herein. In certain embodiments, the protein of interest, such as HIV envelope protein, is loaded at a certain salt concentration and pH, and eluted in purer form at an increased salt concentration and increased pH as compared to the loading conditions.

It is an aspect of the invention to provide a process for purifying HIV-1 gp140 protein, comprising capturing the protein on a multimodal resin comprising hydrophobic interaction and cation exchange properties, and eluting a purified fraction from said resin, wherein the purity of the HIV-1 gp140 protein is substantially increased as compared to the protein in the mixture that was loaded on the resin during the capturing step. Such multimodal resins appear particularly suitable for purification of HIV-1 gp140 protein.

In another aspect of the invention, a process for purifying HIV-1 gp140 protein is provided, the process comprising the steps of:
i) providing a composition comprising HIV-1 gp140 protein and other, non-desired proteins, such as host cell proteins derived from the host cell in which HIV-1 gp140 protein was expressed;
ii) capturing the HIV-1 gp140 protein on a multimodal resin comprising hydrophobic interaction and cation exchange properties, and eluting a purified fraction comprising the HIV-1 gp140 protein from said resin;

iii) applying the purified fraction of step ii) to an anion exchange resin to bind the HIV-1 gp140 protein, and eluting a further purified fraction comprising the HIV-1 gp140 protein from said resin; and iv) subjecting the further purified fraction of step iii) to a mixed mode resin that has anion-exchange and hydrophobic functionalities, and eluting a further purified HIV-1 gp140 protein.

In certain embodiments, the HIV-1 gp140 protein is clade C gp140 protein or mosaic gp140 protein, preferably mosaic gp140 protein.

In certain embodiments, the process further comprises a step of applying the further purified fraction of HIV-1 gp140 protein of step iii) to a resin that comprises dextran sulfate, and eluting a further purified fraction comprising the HIV-1 gp140 protein from said resin, before subjecting this fraction to step iv) of this process. Preferably, the HIV-1 gp140 protein in these embodiments is clade C gp140 protein.

According to the embodiments of the application, the inventive process can be used in both laboratory scale and commercial scale. For example, the process of protein purification can be used to provide purified HIV-1 gp140 proteins for the purpose of investigation study. The process of the application can also be used in commercial and large scale to provide large quantities of purified HIV-1 gp140 proteins, preferably in trimeric state. In particular, large scale of purification of clade C gp140 protein can be achieved using a process described in FIG. 3, and large scale of purification of mosaic gp140 protein can be achieved using a process described in FIG. 4.

Human immunodeficiency virus (HIV) is a member of the genus Lentivirinae, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer, but are not limited to, HIV-1 and HIV-2.

HIV is categorized into multiple clades with a high degree of genetic divergence. As used herein, the term "HIV clade" or "HIV subtype" refers to related human immunodeficiency viruses classified according to their degree of genetic similarity. There are currently three groups of HIV-1 isolates: M, N and O. Group M (major strains) consists of at least ten clades, A through J. Group O (outer strains) can consist of a similar number of clades. Group N is a new HIV-1 isolate that has not been categorized in either group M or O.

As used herein, the terms "HIV antigenic polypeptide," "HIV antigenic protein," "HIV antigen," and "HIV immunogen" refer to a polypeptide capable of inducing an immune response, e.g., a humoral and/or cellular mediated response, against HIV in a subject. The antigenic polypeptide or antigen can be a protein of the HIV, a fragment or epitope thereof, or a combination of multiple HIV proteins or portions thereof that can induce an immune response or produce an immunity, e.g., protective immunity, against the HIV in a subject.

Preferably, an antigenic polypeptide or antigen is capable of raising in a host a protective immune response, e.g., inducing an immune response against a viral disease or infection, and/or producing an immunity in (i.e., vaccinates) a subject against a viral disease or infection, that protects the subject against the viral disease or infection. For example, the antigenic polypeptide or antigen can comprise a protein or fragments thereof from Simian Immunodeficiency Virus (SIV) or an HIV, such as the HIV or SIV envelope gp160 protein, the HIV or SIV matrix/capsid proteins, and the HIV or SIV gag, pol and env gene products.

An HIV antigenic polypeptide or antigen can be any HIV-1 or HIV-2 antigen or fragment thereof. Examples of HIV antigens include, but are not limited to gag, pol, and env gene products, which encode structural proteins and essential enzymes. Gag, pol, and env gene products are synthesized as polyproteins, which are further processed into multiple other protein products. The primary protein product of the gag gene is the viral structural protein gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41. Other examples of HIV antigens include gene regulatory proteins Tat and Rev; accessory proteins Nef, Vpr, Vif and Vpu; capsid proteins, nucleocapsid proteins, and p24 viral protein.

In certain embodiments, the HIV antigenic polypeptide or antigen comprises an HIV Gag, Env, or Pol antigen, or any antigenic portion or epitope or combination thereof, preferably an HIV-1 Gag, Env, or Pol antigen or any antigenic portion or epitope or combination thereof.

HIV antigenic polypeptides can also be mosaic HIV antigens. As used herein, "mosaic antigen" refers to a recombinant protein assembled from fragments of natural sequences. Mosaic antigens resemble natural antigens, but are optimized to maximize the coverage of potential T-cell epitopes found in the natural sequences, which improves the breadth and coverage of the immune response. Mosaic HIV antigens can for instance be mosaic Gag, Pol, and/or Env antigens, and more preferably a mosaic HIV-1 Env antigen. As used herein, "a mosaic HIV Gag, Pol, and/or Env antigen" specifically refers to a mosaic antigen comprising multiple epitopes derived from one or more of the Gag, Pol and/or Env polyprotein sequences of HIV.

As used herein, each of the terms "HIV envelope protein," "env protein," and "Env" refers to a protein that is expressed on the envelope of an HIV virion and enables an HIV to target and attach to the plasma membrane of HIV infected cells, or a fragment or derivative thereof that can induce an immune response or produce an immunity against the HIV in a subject in need thereof. The HIV env gene encodes the precursor protein gp160, which is proteolytically cleaved into the two mature envelope glycoproteins, gp120 and gp41. The cleavage reaction is mediated by a host cell protease, furin, at a sequence highly conserved in retroviral envelope glycoprotein precursors. More specifically, gp160 trimerizes to $(gp160)_3$ and then undergoes cleavage into the two noncovalently associated gp120 and gp41. Viral entry is subsequently mediated by a trimer of gp120/gp41 heterodimers. Gp120 is the receptor binding fragment, and binds to the CD4 receptor on a target cell that has such a receptor, such as, e.g., a T-helper cell. Gp41, which is non-covalently bound to gp120, is the fusion fragment and provides the second step by which HIV enters the cell. Gp41 is originally buried within the viral envelope, but when gp120 binds to a CD4 receptor, gp120 changes its conformation causing gp41 to become exposed, where it can assist in fusion with the host cell. Gp140 is the uncleaved ectodomain of trimeric gp160, i.e., $(gp160)_3$, that has been used as a surrogate for the native state of the cleaved, viral spike.

According to embodiments of the invention, an "HIV envelope protein" can be a gp160, gp140, gp120, gp41 protein, combinations, fusions, truncations or derivatives thereof. For example, an "HIV envelope protein" can include a gp120 protein noncovalently associated with a gp41 protein. It can also include a stabilized trimeric gp140 protein that can have or can be modified to include a trimerization domain that stabilizes trimers of gp140. Examples of trimerization domains include, but are not limited to, the T4-fibritin "foldon" trimerization domain; the coiled-coil trimerization domain derived from GCN4; and the catalytic subunit of *E. coli* aspartate transcarbamoylase as a trimer tag. An "HIV envelope protein" can also be a truncated HIV envelope protein including, but not limited to, envelope proteins comprising a C-terminal truncation in the ectodomain (i.e. the domain that extends into the extracellular space), a truncation in the gp41, such as a truncation in the transmembrane domain of gp41, or a truncation in the cytoplasmic domain of gp41. An "HIV envelope protein" can further be a derivative of a naturally occurring HIV envelope protein having sequence mutations, e.g., in the furin cleavage sites, and/or so-called SOSIP mutations. In preferred embodiments of the invention, HIV envelope protein is a gp140 protein, more preferably HIV-1 clade C gp140 protein or HIV-1 mosaic gp140 protein.

As used herein, each of the terms "stabilized trimeric gp140 protein" and "stabilized trimer of gp140" refers to a trimer of gp140 polypeptides that includes a polypeptide sequence that increases the stability of the trimeric structure. The gp140 polypeptides can have or can be modified to include a trimerization domain that stabilizes trimers of gp140. Examples of trimerization domains include, but are not limited to, the T4-fibritin "foldon" trimerization domain; the coiled-coil trimerization domain derived from GCN4; and the catalytic subunit of *E. coli* aspartate transcarbamoylase as a trimer tag.

Examples of antigenic HIV envelope polypeptides are stabilized trimeric gp140 such as those described in Nkolola et al 2010, *J. Virology* 84(7): 3270-3279; Kovacs et al, *PNAS* 2012, 109(30):12111-6; WO 2010/042942 and WO 2014/107744, all of which are incorporated by reference in their entirety.

In some embodiments of the invention, the "envelope polypeptide" or "envelope glycoprotein" is a mosaic envelope protein comprising multiple epitopes derived from one or more of Env polyprotein sequences of one or more HIV clades. For example, as used herein a "gp140 protein" can be a "mosaic gp140 protein" that contains multiple epitopes derived from one or more gp140 protein sequences of one or more HIV clades. Preferably, a mosaic gp140 protein is a stabilized trimeric gp140 protein.

In a preferred embodiment, a mosaic gp140 protein is a stabilized trimer of mosaic gp140 protein comprising the amino acid sequence of SEQ ID NO: 2.

In some embodiments of the invention, the "envelope polypeptide" or "envelope glycoprotein" is an envelope protein derived from a particular HIV clade, such as HIV clade A, B, or C. For example, as used herein a "gp140 protein" can be a "clade C gp140 protein" that contains envelope protein sequence derived from HIV clade C. Preferably, a clade C gp140 protein is a stabilized trimeric clade C gp140 protein.

In a preferred embodiment, a clade C gp140 protein is a stabilized trimer of clade C gp140 protein comprising the amino acid sequence of SEQ ID NO: 1.

According to certain embodiments of the invention, a gp140 polypeptide, such as a stabilized trimeric gp140 protein can be administered together with viral expression vectors, e.g., adenovirus 26 (see e.g. WO 2016/049287, WO 2017/102929).

In certain embodiments, two gp140 proteins are administered to the same subject, preferably a clade C gp140 having the amino acid sequence of SEQ ID NO: 1 and a mosaic gp140 having the amino acid sequence of SEQ ID NO: 2. These two gp140 proteins can be together in one pharmaceutical composition, preferably administered together with an adjuvant, such as aluminum phosphate adjuvant. A preferred dose for the total amount of gp140 for administration to humans is between about 125 and 350 µg, such as 125, 150, 175, 200, 225, 250, 275, 300, 325, 350 µg, or any amount in between, preferably about 250 µg. If clade C gp140 and mosaic gp140 are both administered, a suitable dose would for instance be about 125 µg of each glycoprotein, to provide a total dose of 250 µg of gp140 glycoprotein for an administration to a human subject. As used herein, unless indicated otherwise, the amount of a gp140 polypeptide refers to the amount of the gp140 polypeptide measured as glycoprotein.

An isolated gp140 protein can be co-delivered or administered in combination with an adenovirus (e.g., Ad26) expression vector or other expression vector such as MVA. According to a preferred embodiment, a gp140 protein and Ad26 or other expression vector are administered separately, as two distinct formulations. Alternatively, a gp140 protein can be administered with Ad26 or other expression vector together in a single formulation. Simultaneous administration or co-delivery can take place at the same time, within one hour, or within the same day. Furthermore, a gp140 protein can be administered in an adjuvanted formulation. Suitable adjuvants can be, for example, aluminum phosphate or a saponin-based adjuvant, preferably aluminum phosphate adjuvant.

Antigenic polypeptides such as gp140 can be produced and isolated using any method known in the art in view of the present disclosure. For example, an antigenic polypeptide can be expressed from a host cell, preferably a recombinant host cell optimized for production of the antigenic polypeptide. According to an embodiment of the invention, a recombinant gene is used to express a gp140 protein containing mutations to eliminate cleavage and fusion activity, preferably an optimized gp140 protein with increased breadth, intensity, depth, or longevity of the antiviral immune response (e.g., cellular or humoral immune responses) generated upon immunization (e.g., when incorporated into a composition, e.g., vaccine) of a subject (e.g., a human). The optimized gp140 protein can also include cleavage site mutation(s), a factor Xa site, and/or a foldon trimerization domain. A leader/signal sequence can be operably linked to the N-terminal of an optimized gp140 protein for maximal protein expression. The leader/signal sequence is usually cleaved from the nascent polypeptide during transport into the lumen of the endoplasmic reticulum. Any leader/signal sequence suitable for a host cell of interest can be used. An exemplary leader/signal sequence comprises the amino acid sequence of SEQ ID NO: 3.

Preferably, an "HIV envelope protein" is a "synthetic HIV envelope protein." As used herein, the term "synthetic HIV envelope protein" refers to a non-naturally occurring HIV envelope protein that is optimized to induce an immune response or produce an immunity against one or more naturally occurring HIV strains in a subject in need thereof. Mosaic HIV Env proteins are examples of synthetic HIV Env proteins, and the invention provides synthetic HIV Env antigens, e.g. the ones comprising SEQ ID NO: 1 or SEQ ID NO: 2.

A protein of interest to be purified by a process according to an embodiment of the application can be expressed by a host cell, preferably a recombinant host cell. In certain embodiments, the protein of interest, such as an HIV envelope protein, can be expressed with a signal sequence, and the signal sequence is cleaved from the nascent polypeptide chain during its transport into the lumen of the endoplasmic reticulum (ER). Any suitable signal sequence could be used. Preferably an HIV Env signal sequence or a variant thereof is used. Different signal sequences have been used in the art for HIV Env proteins (see e.g. WO 2014/107744).

In a preferred embodiment, a protein of interest is recombinantly produced from a host cell transfected with an expression vector comprising nucleic acid sequence encoding the protein, such as an HIV envelope protein. Any suitable expression vectors can be used for recombinant protein expression, including, but not limited to, non-viral vectors, such as plasmids, cosmids, bacterial artificial chromosomes, yeast artificial chromosomes, bacteriophages, etc., or viral vectors, such as adenoviral vectors, adeno-associated virus vectors, baculovirus vectors, poxvirus vectors, MVA vectors, enteric virus vectors, Venezuelan Equine Encephalitis virus vectors, Semliki Forest Virus vectors, Tobacco Mosaic Virus vectors, lentiviral vectors, etc.

The nucleic acid sequence encoding the synthetic HIV envelope protein can be operably linked to a promoter, meaning that the nucleic acid is under the control of a promoter. The promoter can be a homologous promoter (i.e., derived from the same genetic source as the vector) or a heterologous promoter (i.e., derived from a different vector or genetic source). Non-limiting examples of suitable promoters for the adenoviral vectors include the cytomegalovirus (CMV) immediate early promoter and the Rous Sarcoma virus (RSV) promoter. Preferably, the promoter is located upstream of the nucleic acid within an expression cassette.

A host cell is typically used to produce sufficient amounts of protein for use in the invention.

According to a preferred embodiment, a cell of a suitable cell culture can be transformed or transfected with an expression vector. Any host cells, preferably eukaryotic host cells, more preferably mammalian host cells, can be used for recombinant protein expression, including but not limited to PER.C6, HEK293, CHO cells, etc. transfected with an expression vector encoding a protein of interest. The expression vector usually also contains a cassette comprising a marker and/or selection gene that facilitate the identification and isolation of the recombinant host cells expressing the protein of interest. However, a recombinant host cell can also be identified by PCR technology. In certain embodiments, the nucleic acid that encodes the recombinant protein, e.g. HIV envelope protein, is incorporated into the genome of the host cell. This allows production of the recombinant protein from a stable host cell line.

In view of the degeneracy of the genetic code, the skilled person is well aware that several nucleic acid sequences can be designed that encode the same protein, according to methods entirely routine in the art. The nucleic acid encoding a protein of interest, such as an HIV envelope protein, can optionally be codon-optimized to ensure proper expression in the host cell. Codon-optimization is a technology widely applied in the art.

Accordingly, a method of the invention can further comprise producing a protein of interest, such as an HIV antigenic polypeptide, from a recombinant host cell. Preferably, the method comprises transfecting a host cell with an expression vector comprising nucleic acid encoding the HIV antigenic polypeptide operably linked to a promoter, growing the transfected cell under conditions suitable for expression of the synthetic HIV antigenic polypeptide, and isolating the synthetic HIV antigenic polypeptide from the cell using a process of the invention. Techniques used for recombinant protein expression are well known to one of ordinary skill in the art in view of the present disclosure.

Another general aspect of the invention relates to a pharmaceutical composition, such as a vaccine or an immunogenic composition, comprising a protein purified by a process of the invention, and a carrier. A carrier can include one or more pharmaceutically acceptable excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the invention can be formulated in any matter suitable for administration to a subject to facilitate administration and improve efficacy, including, but not limited to, oral (enteral) administration and parenteral injections. The parenteral injections include intravenous injection or infusion, intra-arterial injection, subcutaneous injection, intramuscular injection, and intra-articular injection. Compositions of the invention can also be formulated for other routes of administration including transmucosal, ocular, rectal, long acting implantation, sublingual administration, under the tongue, from oral mucosa bypassing the portal circulation, inhalation, or intranasal.

According to certain embodiments of the invention, a composition comprises an immunogenically effective amount of a protein, such as an HIV envelope protein, purified by a method of the invention, and optionally one or more additional HIV antigens and/or adjuvants. Said compositions can be formulated as a vaccine (also referred to as an "immunogenic composition") according to methods known in the art in view of the present disclosure. In general, when used with reference to a polypeptide, such as an isolated antigenic polypeptide, an immunogenically effective amount can range from, e.g. about 0.3 to about 3000 microgram (μg), e.g. 1-1000 μg, e.g. 10-500 μg, e.g. about 50 or 250 μg.

In some embodiments, compositions of the invention can further optionally comprise an adjuvant to enhance immune responses. The terms "adjuvant" and "immune stimulant" are used interchangeably herein, and are defined as one or more substances that cause stimulation of the immune system. In this context, an adjuvant is used to enhance an immune response to the vectors encoding synthetic HIV envelope proteins of the invention and optionally one or more additional HIV antigens and/or HIV antigenic polypeptides used in combination with vectors encoding synthetic HIV envelope proteins of the invention and optionally one or more additional HIV antigens.

Adjuvants suitable for use with the invention should be ones that are potentially safe, well tolerated and effective in people, such as for instance QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, aluminum salts (e.g. AdjuPhos), Adjuplex, and MF59. The optimal ratios of each component in the formulation can be determined by techniques well known to those skilled in the art in view of the present disclosure.

In a preferred embodiment, the adjuvant is an aluminum salt, such as aluminum hydroxide or aluminum phosphate, e.g. AdjuPhos. In certain embodiments, the aluminum phosphate is preferably present in or administered with a composition with isolated HIV antigenic polypeptide, such as gp140.

The preparation and use of immunogenic compositions are well known to those of ordinary skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can also be included.

Alternatively, the vaccine shots can be prepared by stepwise, freeze-drying of the virus in a formulation. In certain embodiments, the formulation contains additional additives such as mannitol, dextran, sugar, glycine, lactose, polyvinylpyrrolidone, or other additives, such as, including, but not limited to, antioxidants or inert gas, stabilizers or recombinant proteins (e.g. human serum albumin) suitable for in vivo administration. The ampoule is then sealed and can be stored at a suitable temperature, for example, between 4° C. and room temperature for several months. However, as long as no need exists, the ampoule is stored preferably at temperatures below −20° C.

In various embodiments involving vaccination or therapy, the lyophilisate is dissolved in 0.1 to 0.5 ml of an aqueous solution, preferably physiological saline or tris(hydroxymethyl)aminomethane (Tris) buffer, and administered either systemically or locally, i.e., by parenteral, subcutaneous, intravenous, intramuscular, intranasal, intradermal, or any other path of administration known to a skilled practitioner. Optimization of the mode of administration, dose, and number of administrations is within the skill and knowledge of one skilled in the art.

In certain embodiments, the HIV envelope proteins such as gp140 proteins made by methods according to the invention are included into a composition comprising sorbitol (e.g. 2 to 15% (w/v), e.g. 5% or 12%), polysorbate 20 (e.g. 0.01 to 0.05% (w/v), e.g. 0.02%), and histidine buffer (e.g. 5 to 20 mM, pH 5.5 to 7.0, e.g. 10 mM at pH 6.5), see e.g. WO 2017/216288. Such compositions can optionally further comprise an adjuvant, e.g. aluminum phosphate (e.g. 0.7-4.0 mg/mL, e.g. 0.7-1 mg/mL, e.g. 085 mg/mL). The HIV envelope proteins can for instance be present at a concentration of about 0.05-5 mg/mL, e.g. 0.2 mg/mL or 1 mg/mL. Such compositions can be stored at for instance between about −80° to about 25° C., e.g. at about −80° C., −60° C., −20°, or preferably at about 2-8° C., which provides for stable liquid compositions that are directly usable for administration as vaccines.

The invention also relates to a method of inducing an immune response against one or more HIV clades in a subject in need thereof using a pharmaceutical composition or vaccine of the invention. According to embodiments of the invention, "inducing an immune response" when used with reference to the methods and compositions described herein encompasses providing protective immunity and/or vaccinating a subject against an infection, such as a HIV infection, for prophylactic purposes, as well as causing a desired immune response or effect in a subject in need thereof against an infection, such as a HIV infection, for therapeutic purposes, i.e., therapeutic vaccination. "Inducing an immune response" also encompasses providing a therapeutic immunity for treating against a pathogenic agent, i.e., HIV. Typically, for prophylactic vaccination, compositions and vaccines are administered to subjects who have not been previously infected with HIV, whereas for therapeutic vaccination, compositions and vaccines are administered to a subject already infected with HIV. The immune response can be a cellular immune response and/or a humoral immune response.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

As used herein, the term "therapeutic immunity" or "therapeutic immune response" means that the HIV infected vaccinated subject is able to control an infection with the pathogenic agent, i.e., HIV, against which the vaccination was done. In certain embodiments, the methods of inducing an immune response according to the invention are for therapeutic purposes, such as for therapeutic vaccination, in which the compositions and vaccines described herein are administered to a subject already infected with HIV. The terms "HIV infection" and "HIV-infected" as used herein refer to invasion of a human host by HIV. As used herein, "an HIV-infected subject" refers to a subject in whom HIV has invaded and subsequently replicated and propagated within the host, thus causing the host to be infected with HIV or have an HIV infection or symptoms thereof. In other embodiments, the proteins and compositions of the invention can be used for prophylactic vaccination, e.g. by administration to a subject, preferably a human subject, that is not HIV infected.

Administration of an immunogenic compositions comprising an antigenic polypeptide is typically intramuscular, intradermal or subcutaneous. However, other modes of administration such as intravenous, rectal, cutaneous, oral, nasal, etc. can be envisaged as well. Intramuscular administration of the immunogenic compositions can be achieved by using a needle to inject a suspension of the antigenic polypeptides. An alternative is the use of a needleless injection device to administer the composition (using, e.g., Biojector™) or a freeze-dried powder containing the vaccine.

For intramuscular, intravenous, cutaneous or subcutaneous injection, or injection at the site of affliction, the isolated antigenic polypeptide will typically be in the form of a parenterally acceptable solution having a suitable pH, isotonicity, and stability. Those of ordinary skill in the art are well able to prepare suitable solutions using, for example, isotonic vehicles such as Sodium Chloride Injection, Ringer's Injection, and Lactated Ringer's Injection. Preservatives, stabilizers, buffers, antioxidants and/or other additives can be included, as required. A slow-release formulation can also be employed. Examples of suitable formulations for HIV gp140 proteins are provided in WO 2017/216288, incorporated by reference herein.

An amount of a composition sufficient to induce a detectable immune response is defined to be an "immunogenically effective dose" or "immunogenically effective amount." The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in generally available textbooks and manuals.

EXAMPLES

Upstream and downstream process for the production and purification of a recombinant protein (e.g., gp140 of Clade C HIV (SEQ ID NO:1) or mosaic HIV gp140 (SEQ ID NO: 2)) expressed by recombinant PER. C6 cell lines were studied. Multiple growth media were tested to improve gene expression and productivity of the recombinant host cell in a bioreactor. For example, the feed to the bioreactor was concentrated by 20% to allow for increased productivity.

Various processes, conditions and columns were studied for purification of the protein of interest (e.g., gp140 of Clade C HIV or mosaic HIV gp140), with the goals to, e.g., minimize final host cell protein (HCP) levels, maintain product variant level and/or conformation, eliminate DNA and other contaminations, and with relatively high yield (e.g., at least about 10%, preferably at least about 15% overall yield). Using the processes of the invention, HCP levels in the final gp140 protein product were reduced below 5000 ppm, typically below 1000 ppm, and host cell DNA was below detection levels.

Due to the high cell density and cell type of the recombinant host cells, it was difficult to filter harvests of the cells. Gravity based cell settling is not feasible for large scale production of the protein of interest. Thus, a continuous centrifugation was used to replace the gravity-settled step.

It was noticed that precipitation occurred after the first ultrafiltration in preparation for loading onto the 1st purification column (being a mixed mode resin comprising hydrophobic interaction and cation exchange properties, which surprisingly was found to be the most suitable capture column from a wide variety of possibilities). Acid precipitation (or low pH flocculation) and depth filtration were used to remove cell debris and other precipitates while maintaining sufficient amount of the protein of interest (e.g., HIV gp140) in the filtrate, prior to the first ultrafiltration to avoid fouling of the filter membranes by the precipitates. It was shown that, the turbidity of the clarified harvest material adjusted to pH 5.0 +/−0.1 (e.g., with 1 M acetic acid) reached a plateau of about 70 nephelometric turbidity units (NTU) after about 3 hours incubation but reached >95% of the final NTU (see, e.g., FIGS. 1A and 1B). Although large precipitation was visible during the acid precipitation, recovery yield of the recombinant protein was also high, e.g., about 100% for Clade C gp140, suggesting that no or minimal amount of Clade C gp140 precipitated out or lost during the acid precipitation. The acid precipitate materials were filtered through various depth filters for selection of filters and the turbidity was again measured after filtration. Suitable filters gave significant reduction in turbidity and removal of HCPs, but with no significant loss in the recombinant protein.

Figure 1B:
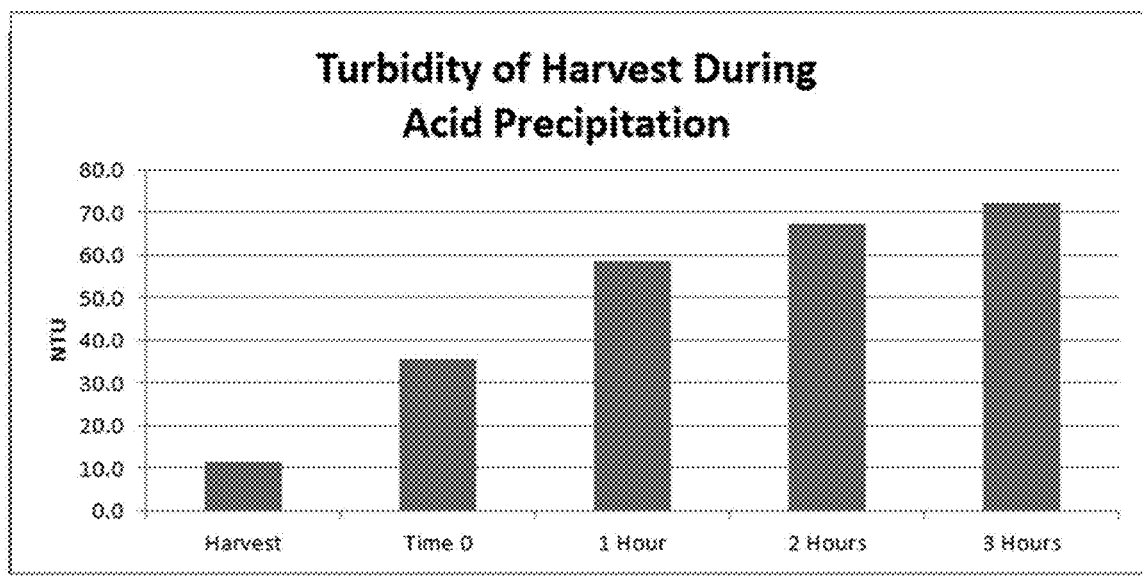
FIG. 1B shows increased turbidity of harvest during acid precipitation.

Ultrafiltration (UF) and diafiltration (DF) are used for product concentration and buffer exchange before column separation (FIG. 1A). The UF/DF prepared the product for the following chromatography stage. Columns are often operating under different pH or molarity conditions and the product needs to be primed for chromatography use beforehand by the UF and DF. Suitable UF/DF can be selected in view of the disclosure in the application.

Figure 2A:
FIGS. 2A and 2B show that using a process illustrated in FIG. 2A, desired minimal levels of host cell protein (HCP) were achieved in the purified products (FIG. 2B); for HIV-1 clade C gp140, an example for the columns used during the illustrated chromatography steps is: chrom #1 (capture step using a mixed mode resin comprising hydrophobic interaction and cation exchange properties), chrom #2 (anion exchange resin), chrom #3 (resin that comprises the ligand dextran sulfate), chrom #4 (mixed mode resin that has anion-exchange and hydrophobic functionalities)
Figure 2B:
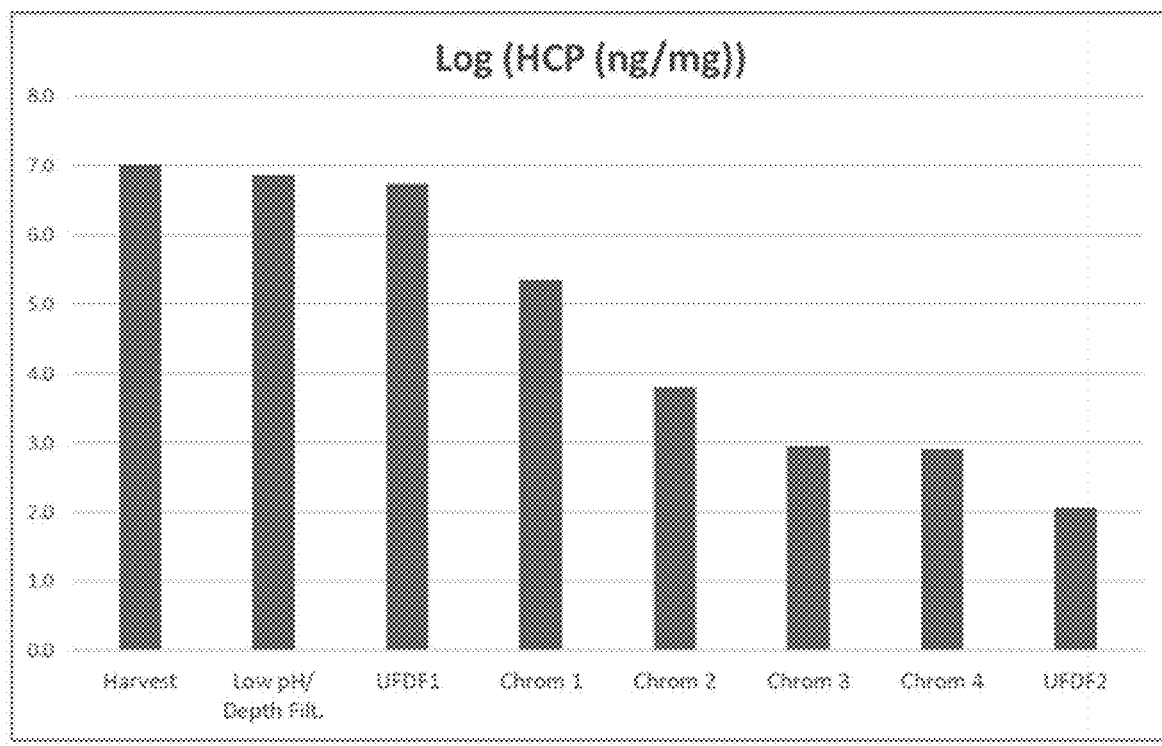

A process of the invention comprises three or more chromatographic column steps, which can be preceded by UF/DF of the product. Various resins were assessed through screening methods, in view of the unpredictability of a suitable combination of columns for a given specific protein, with the aim of fulfilling the requirements of sufficient yield and high purity during a large scale manufacturing process. Binding isotherms were generated to assess product impurity binding. Different columns were studied and compared. Columns with the greatest binding capacity were viewed as "capture" columns. Using a purification process illustrated in FIG. 2A, desired low level of HCP was achieved (FIG. 2B).

Further improvement to the process was made to optimize the scale-up production. Development efforts focusing on facility fit and process robustness were conducted. Such efforts include, for example, feed variance, seed density, pH sensitivities, bioreactor temperature, pCO2 variation, reactor duration, etc. Pilot scale, scale down model and engineering principles were used to show readiness of the process for good manufacturing practice (GMP) production.

Excellent results were found for purification of the clade C gp140 protein using a process described in FIG. 3, and for purification of mosaic gp140 protein using a process described in FIG. 4. These processes were found suitable for large scale manufacturing of pharmaceutical grade products.

Example 1

Purification of Clade C gp140

Clade C gp140 was manufactured by a fed batch cell culture process. The expansion of cells and the production of Clade C gp140 occurred in the first 2 stages of the process, including Stage 1 (preculture and seed bioreactor) which uses a PER.C6 cell line that expresses Clade C gp140, and Stage 2 (production in a bioreactor with volume of 15,000 L to 16,500 L). The subsequent purification and manufacture of formulated bulk (FB) occurred in the remaining 11 stages. A flow diagram of the Clade C gp140 drug substance manufacturing process from preculture and expansion through drug substance (DS) is shown in FIG. 3.

The target run duration of the 15,000 L production process is 18 days. The contents of the 15,000 L production then undergo flocculation by adjustment with 25% acetic acid to a target of pH 4.8 (Stage 3, low pH flocculation). The flocculation is followed by clarification (Stage 4) through centrifugation and depth/polish filtration. The subsequent ultrafiltration and diafiltration (UFDF) step (Stage 5) was conducted in a solution containing 50 mM tris(hydroxymethyl)aminomethane (Tris) and 150 mM sodium chloride at pH 7.6 to obtain a pooled UFDF retentate.

In Stage 6, the pH of the pooled UFDF retentate was adjusted with 1M acetic acid to 5.0. Then the retentate was loaded to a column of Capto MMC ImpRes, which was already equilibrated with a solution containing 50 mM sodium acetate at pH 5.0. This Capto MMC ImpRes column chromatography was performed in bind and elute mode in order to remove host cell proteins and potentially present DNA. The Clade C gp140 bound to the column and was eluted later by an elution solution containing 50 mM 2-[4-(2-hydroxyethyl)piperazin-1-yl]ethanesulfonic acid (HEPES) and 400 mM sodium chloride at pH 7.0 to obtain a pooled elute.

In Stage 7, the pooled elute collected from the above Capto MMC ImpRes chromatography step was neutralized with 1M Tris (pH 9.0) to pH 7.5 and then diluted with water for injection (to a conductivity of less than 6 mS/cm). The resulting pH-adjusted and diluted elute was loaded to a column of POROS 50 HQ, which was already equilibrated with a solution containing 25 mM Tris at pH 7.5. This POROS 50 HQ column chromatography was performed in bind and elute mode to further remove host cell proteins and potentially DNA. The Clade C gp140 bound to the column and was eluted later by an elution solution containing 25 mM Tris and 185 mM sodium chloride at pH 7.5 (conductivity about 19 mS/cm) to obtain a pooled elute.

In Stage 8, the pooled elute collected from the above POROS 50 HQ chromatography step was adjusted with 1M acetic acid to pH 6.5 and then diluted with water for injection (to a conductivity of less than 7 mS/cm). The resulting pH-adjusted and diluted elute was loaded to a column of Capto DeVirS, which was already equilibrated with a solution containing 20 mM HEPES and 50 mM sodium chloride at pH 6.5. This Capto DeVirS column chromatography was performed in bind and elute mode. The Clade C gp140 bound to the column and was eluted later by an elution solution containing 25 mM Tris and 185 mM sodium chloride at pH 7.5 (conductivity about 19 mS/cm) to obtain a pooled elute.

In Stage 9, 5M sodium chloride was added to the pooled eluate collected from the above Capto DeVirS chromatography step to adjust its conductivity to be 62 mS/cm, adjusted with 1M acetic acid to pH 3.5 for viral inactivation, neutralized with 1M Tris (pH 9.0) to pH 4.5, and then diluted with water for injection to a conductivity of 30 mS/cm.

In Stage 10, the diluted elute obtained from Stage 9 was loaded to a column of Capto Adhere, which was already equilibrated with a solution containing 50 mM sodium acetate and 317 mM sodium chloride at pH 4.5. This Capto Adhere column chromatography was performed in flow-through mode to remove potentially present nucleic acids and host cell proteins, and the flow-through solution contains the clade C gp140 protein in 50 mM sodium acetate and 317 mM sodium chloride at pH 4.5.

In Stage 11, the eluate (actually being the flow-through) collected from the above Capto Adhere chromatography step was neutralized with 1M Tris (pH 9.0) to be pH 6.5, and then was processed through a Planova 20N viral filter for viral retentive filtration. The obtained filtrate was subjected to final ultrafiltration and diafiltration (UFDF) into the formulation buffer (Stage 12) and final formulation of the drug substance (Stage 13).

The purification process also included the in-process control (IPC) tests performed during each process stage of the manufacturing process. The IPC tests were defined as tests, checks and measurements made during the course of manufacturing to monitor and, if necessary, adjust the process to ensure that the resulting API or finished product would comply with its specification. The remaining in-process tests were defined as Process Monitoring tests (PMT's) and are tests, checks, and measurements performed during the course of routine production to monitor the process to assure that the process remains in a state of control.

Example 2

Purification of Mosaic gp140

A flow diagram of the Mosaic gp140 drug substance manufacturing process from preculture and expansion through drug substance (DS) is shown in FIG. 4. The large scale manufacture of Mosaic gp140 includes Stage 1 (preculture and seed bioreactor), Stage 2 (2000 L production in single use bioreactor (SUB)), Stage 3 (pH 5 flocculation) and Stage 4 (clarification) processes. The preculture process uses a PER.C6 cell line that expresses mosaic gp140 and entails expansion from vial thaw through shake flasks, wave bags and the 500 L Seed Bioreactor. The maximum duration of Stage 1 is 40 days for preculture including the seed bioreactor. Then the batch is transferred to the 2000 L production SUB process (Stage 2) after inoculation. The target run duration of the 2000 L production SUB process is 19 days. The contents of the 2000 L production SUB then undergo flocculation by adjustment with 1M acetic acid to a target of pH 5.0 (Stage 3). The flocculation is followed by clarification (Stage 4) through centrifugation, depth filtration and polish filtration, or through depth filtration and polish filtration only.

In Stage 5, the obtained filtrate was adjusted with 1M Tris (pH 9) and 5M sodium chloride to pH 5.25 with a conductivity of 15 mS/cm, and then loaded to a column of Capto MMC ImpRes, which was already equilibrated with 50 mM sodium acetate at pH 5.0. This Capto MMC ImpRes column chromatography was performed in bind and elute mode in order to remove host cell proteins and potentially present DNA. The mosaic gp140 bound to the column and was eluted later by an elution solution containing 50 mM HEPES and 400 mM sodium chloride at pH 7.0 to obtain a pooled elute.

In Stage 6, the pooled elute collected from the above Capto MMC ImpRes chromatography step was neutralized with 1M Tris (pH 9.0) and then diluted with water for injection to obtain a pooled elute at pH 8.0 with a conductivity of 5.5 mS/cm. The resulting pH-adjusted and diluted elute was loaded to a column of POROS 50 HQ, which was already equilibrated with a solution containing 50 mM Tris at pH 8.0. This POROS 50 HQ column chromatography was performed in bind and elute mode to further remove host cell proteins and potentially present DNA. The mosaic gp140 bound to the column and was eluted later by gradient elution 6%-42% of buffer B with gradient length=11.0 CV, wherein buffer A was 50 mM Tris at pH 8.0, and buffer B was a mixture of 50 mM Tris and 500 mM sodium chloride at pH 8.0, and the conductivity was increased from about 6 to 20 mS/cm.

In Stage 7, the pooled eluate collected from the above POROS 50 HQ chromatography step was added 5M sodium chloride to adjust the conductivity of the pooled eluate to be 56 mS/cm, and adjusted with 1M acetic acid to pH 3.5 for viral inactivation.

In Stage 8, the elute obtained from Stage 7 was loaded to a column of Capto Adhere, which was already equilibrated with a solution containing 50 mM sodium acetate and 650 mM sodium chloride at pH 3.5. This Capto Adhere column chromatography was performed in flow-through mode to remove potentially present nucleic acids and host cell proteins. The pooled eluate was neutralized with 1M Tris (pH 9.0) to pH 6.5.

In Stage 9, the neutralized elute was processed through a Planova 20N viral filter for viral retentive filtration. The obtained filtrate was subjected to final ultrafiltration and diafiltration (UFDF) into the formulation buffer (Stage 10) and final formulation of the drug substance (Stage 11).

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

TABLE 1

| Sequences HIV-1 envelope proteins |
|---|
| SEQ ID NO: 1 clade C gp140 protein (679 amino acids) |
| AENLWVGNMW VTVYYGVPVW TDAKTTLFCA SDTKAYDREV |
| HNVWATHACV PTDPNPQEIV LENVTENFNM WKNDMVDQMH |
| EDIISLWDQS LKPCVKLTPL CVTLHCTNAT FKNNVTNDMN |
| KEIRNCSFNT TTEIRDKKQQ GYALFYRPDI VLLKENRNNS |
| NNSEYILINC NASTITQACP KVNFDPIPIH YCAPAGYAIL |
| KCNNKTFSGK GPCNNVSTVQ CTHGIKPVVS TQLLLNGSLA |
| EKEIIIRSEN LTDNVKTIIV HLNKSVEIVC TRPNNNTRKS |
| MRIGPGQTFY ATGDIIGDIR QAYCNISGSK WNETLKRVKE |
| KLQENYNNNK TIKFAPSSGG DLEITTHSFN CRGEFFYCNT |
| TRLFNNNATE DETITLPCRI KQIINMWQGV GRAMYAPPIA |
| GNITCKSNIT GLLLVRDGGE DNKTEEIFRP GGGNMKDNWR |
| SELYKYKVIE LKPLGIAPTG AKERVVEREE RAVGIGAVFL |
| GFLGAAGSTM GAASLTLTVQ ARQLLSSIVQ QQSNLLRAIE |
| AQQHMLQLTV WGIKQLQTRV LAIERYLKDQ QLLGIWGCSG |
| KLICTTNVPW NSSWSNKSQT DIWNNMTWME WDREISNYTD |
| TIYRLLEDSQ TQQEKNEKDL LALDSWKNLW SWFDISNWLW |

TABLE 1-continued

| Sequences HIV-1 envelope proteins |
|---|
| YIKSRIEGRG SGGYIPEAPR DGQAYVRKDG EWVLLSTFL |
| SEQ ID NO: 2 mosaic gp140 protein (695 amino acids) |
| AGKLWVTVYY GVPVWKEATT TLFCASDAKA YDTEVHNVWA |
| THACVPTDPN PQEVVLENVT ENFNMWKNNM VEQMHEDIIS |
| LWDQSLKPCV KLTPLCVTLN CTDDVRNVTN NATNTNSSWG |
| EPMEKGEIKN CSFNITTSIR NKVQKQYALF YKLDVVPIDN |
| DSNNTNYRLI SCNTSVITQA CPKVSFEPIP IHYCAPAGFA |
| ILKCNDKKFN GTGPCTNVST VQCTHGIRPV VSTQLLLNGS |
| LAEEEVVIRS ENFTNNAKTI MVQLNVSVEI NCTRPNNNTR |
| KSIHIGPGRA FYTAGDIIGD IRQAHCNISR ANWNNTLRQI |
| VEKLGKQEGN NKTIVFNHSS GGDPEIVMHS FNCGGEFFYC |
| NSTKLFNSTW TWNNSTWNNT KRSNDTEEHI TLPCRIKQII |
| NMWQEVGKAM YAPPIRGQIR CSSNITGLLL TRDGGNDTSG |
| TEIFRPGGGD MRDNWRSELY KYKVVKIEPL GVAPTKAKER |
| VVQREERAVG IGAVFLGFLG AAGSTMGAAS MTLTVQARLL |
| LSGIVQQQNN LLRAIEAQQH LLQLTVWGIK QLQARVLAVE |
| RYLKDQQLLG IWGCSGKLIC TTTVPWNASW SNKSLDKIWN |
| NMTWMEWERE INNYTSLIYT LIEESQNQQE KNEQELLELD |
| KWASLWNWFD ISNWLWYIKS RIEGRGSGGY IPEAPRDGQA |
| YVRKDGEWVL LSTFL |
| SEQ ID NO: 3 (exemplary leader sequence) - amino acids |
| MRVRGIQRNC QHLWRWGTLI LGMLMICSA |

The invention claimed is:

1. A process for purifying HIV-1 gp140 protein, comprising the steps of:

i) providing a composition comprising HIV-1 gp140 protein and other, non-desired host cell proteins derived from the host cell in which HIV-1 gp140 protein is expressed;

ii) capturing the HIV-1 gp140 protein on a multimodal resin comprising hydrophobic interaction and cation exchange properties, and eluting a purified fraction comprising the HIV-1 gp140 protein from the multimodal resin, wherein the multimodal resin comprising hydrophobic interaction and cation exchange properties comprises a solid support matrix with the following attached ligand of 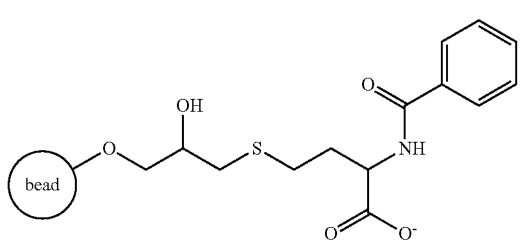 or

;

iii) applying the purified fraction of step ii) to an anion exchange resin to bind the HIV-1 gp140 protein, and eluting a further purified fraction comprising the HIV-1 gp140 protein from the anion exchange resin, wherein the anion exchange resin comprises a solid support matrix with a ligand of quaternary polyethyleneimine;

iv) applying the further purified fraction of HIV-1 gp140 protein of step iii) to an affinity medium resin comprising the ligand dextran sulfate, and eluting a further purified fraction comprising the HIV-1 gp140 protein from said resin; and, v) subjecting the further purified fraction of step iii) to a multimodal resin that has anion-exchange and hydrophobic functionalities, wherein the multimodal resin that has anion-exchange and hydrophobic functionalities comprises a solid support matrix with a ligand of

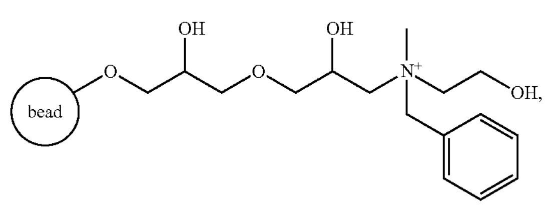 [SMILES: COCC(O)COCC(O)C[N+](C)(CCO)Cc1ccccc1]

, and eluting a further purified HIV-1 gp140 protein.

2. The process of claim 1, wherein the HIV-1 gp140 protein is clade C gp140 protein.

3. The process of claim 1, wherein the HIV-1 gp140 protein binds to the multimodal resin in step ii) and is eluted later.

4. The process of claim 1, wherein the multimodal resin in step iv) is used in flow-through mode.

5. The process of claim 1, wherein the HIV-1 gp140 protein is mosaic gp140 protein.

6. The process of claim 1, wherein the HIV-1 gp140 protein binds to the affinity medium resin and is eluted later.

7. The process of claim 1, wherein the composition in step i) is produced by host cells in a bioreactor.

8. The process of claim 7, wherein the bioreactor has a volume of between 1 L to 20000 L.

9. The process of claim 1, wherein the process further comprises adjusting the pH of the composition to 5.0 to thereby precipitate host cell proteins (HCPs) in the composition before step i).

10. The process of claim 1, wherein the purified HIV-1 gp140 protein is subject to a viral retentive filtration step.

11. The process of claim 1, wherein the purified HIV-1 gp140 protein is subject to ultrafiltration (UF) and diafiltration (DF).

12. The process of claim 1, wherein the purified HIV-1 gp140 protein is subject to a final formulation step.

13. The process of claim 2, wherein the HIV-1 gp140 protein is clade C gp140 protein comprises SEQ ID NO: 1.

14. The process of claim 5, wherein the HIV-1 gp140 protein is mosaic gp140 protein comprising SEQ ID NO: 2.

\* \* \* \* \*

SEQUENCE LISTING

```
<160> NUMBER OF SEQ ID NOS: 3

<210> SEQ ID NO 1
<211> LENGTH: 679
<212> TYPE: PRT
<213> ORGANISM: Artificial Sequence
<220> FEATURE:
<223> OTHER INFORMATION: HIV clade C gp140 protein

<400> SEQUENCE: 1
```

Ala Glu Asn Leu Trp Val Gly Asn Met Trp Val Thr Val Tyr Tyr Gly
1               5                   10                  15

Val Pro Val Trp Thr Asp Ala Lys Thr Thr Leu Phe Cys Ala Ser Asp
            20                  25                  30

Thr Lys Ala Tyr Asp Arg Glu Val His Asn Val Trp Ala Thr His Ala
        35                  40                  45

Cys Val Pro Thr Asp Pro Asn Pro Gln Glu Ile Val Leu Glu Asn Val
    50                  55                  60

Thr Glu Asn Phe Asn Met Trp Lys Asn Asp Met Val Asp Gln Met His
65                  70                  75                  80

```
Glu Asp Ile Ile Ser Leu Trp Asp Gln Ser Leu Lys Pro Cys Val Lys
                85                  90                  95
Leu Thr Pro Leu Cys Val Thr Leu His Cys Thr Asn Ala Thr Phe Lys
                100                 105                 110
Asn Asn Val Thr Asn Asp Met Asn Lys Glu Ile Arg Asn Cys Ser Phe
                115                 120                 125
Asn Thr Thr Thr Glu Ile Arg Asp Lys Gln Gln Gly Tyr Ala Leu
            130                 135                 140
Phe Tyr Arg Pro Asp Ile Val Leu Leu Lys Glu Asn Arg Asn Asn Ser
145                 150                 155                 160
Asn Asn Ser Glu Tyr Ile Leu Ile Asn Cys Asn Ala Ser Thr Ile Thr
                165                 170                 175
Gln Ala Cys Pro Lys Val Asn Phe Asp Pro Ile Pro Ile His Tyr Cys
                180                 185                 190
Ala Pro Ala Gly Tyr Ala Ile Leu Lys Cys Asn Asn Lys Thr Phe Ser
                195                 200                 205
Gly Lys Gly Pro Cys Asn Asn Val Ser Thr Val Gln Cys Thr His Gly
                210                 215                 220
Ile Lys Pro Val Val Ser Thr Gln Leu Leu Asn Gly Ser Leu Ala
225                 230                 235                 240
Glu Lys Glu Ile Ile Ile Arg Ser Glu Asn Leu Thr Asp Asn Val Lys
                245                 250                 255
Thr Ile Ile Val His Leu Asn Lys Ser Val Glu Ile Val Cys Thr Arg
                260                 265                 270
Pro Asn Asn Asn Thr Arg Lys Ser Met Arg Ile Gly Pro Gly Gln Thr
                275                 280                 285
Phe Tyr Ala Thr Gly Asp Ile Ile Gly Asp Ile Arg Gln Ala Tyr Cys
290                 295                 300
Asn Ile Ser Gly Ser Lys Trp Asn Glu Thr Leu Lys Arg Val Lys Glu
305                 310                 315                 320
Lys Leu Gln Glu Asn Tyr Asn Asn Lys Thr Ile Lys Phe Ala Pro
                325                 330                 335
Ser Ser Gly Gly Asp Leu Glu Ile Thr Thr His Ser Phe Asn Cys Arg
                340                 345                 350
Gly Glu Phe Phe Tyr Cys Asn Thr Thr Arg Leu Phe Asn Asn Asn Ala
                355                 360                 365
Thr Glu Asp Glu Thr Ile Thr Leu Pro Cys Arg Ile Lys Gln Ile Ile
        370                 375                 380
Asn Met Trp Gln Gly Val Gly Arg Ala Met Tyr Ala Pro Pro Ile Ala
385                 390                 395                 400
Gly Asn Ile Thr Cys Lys Ser Asn Ile Thr Gly Leu Leu Leu Val Arg
                405                 410                 415
Asp Gly Gly Glu Asp Asn Lys Thr Glu Glu Ile Phe Arg Pro Gly Gly
                420                 425                 430
Gly Asn Met Lys Asp Asn Trp Arg Ser Glu Leu Tyr Lys Tyr Lys Val
                435                 440                 445
Ile Glu Leu Lys Pro Leu Gly Ile Ala Pro Thr Gly Ala Lys Glu Arg
        450                 455                 460
Val Val Glu Arg Glu Glu Arg Ala Val Gly Ile Gly Ala Val Phe Leu
465                 470                 475                 480
Gly Phe Leu Gly Ala Ala Gly Ser Thr Met Gly Ala Ala Ser Leu Thr
                485                 490                 495
```

```
Leu Thr Val Gln Ala Arg Gln Leu Leu Ser Ser Ile Val Gln Gln
            500                 505                 510
Ser Asn Leu Leu Arg Ala Ile Glu Ala Gln Gln His Met Leu Gln Leu
515                 520                 525
Thr Val Trp Gly Ile Lys Gln Leu Gln Thr Arg Val Leu Ala Ile Glu
            530                 535                 540
Arg Tyr Leu Lys Asp Gln Gln Leu Leu Gly Ile Trp Gly Cys Ser Gly
545                 550                 555                 560
Lys Leu Ile Cys Thr Thr Asn Val Pro Trp Asn Ser Trp Ser Asn
            565                 570                 575
Lys Ser Gln Thr Asp Ile Trp Asn Asn Met Thr Trp Met Glu Trp Asp
                580                 585                 590
Arg Glu Ile Ser Asn Tyr Thr Asp Thr Ile Tyr Arg Leu Leu Glu Asp
            595                 600                 605
Ser Gln Thr Gln Gln Glu Lys Asn Glu Lys Asp Leu Leu Ala Leu Asp
610                 615                 620
Ser Trp Lys Asn Leu Trp Ser Trp Phe Asp Ile Ser Asn Trp Leu Trp
625                 630                 635                 640
Tyr Ile Lys Ser Arg Ile Glu Gly Arg Gly Ser Gly Gly Tyr Ile Pro
            645                 650                 655
Glu Ala Pro Arg Asp Gly Gln Ala Tyr Val Arg Lys Asp Gly Glu Trp
                660                 665                 670
Val Leu Leu Ser Thr Phe Leu
            675

<210> SEQ ID NO 2
<211> LENGTH: 695
<212> TYPE: PRT
<213> ORGANISM: Artificial Sequence
<220> FEATURE:
<223> OTHER INFORMATION: HIV mosaic gp140 protein

<400> SEQUENCE: 2

Ala Gly Lys Leu Trp Val Thr Val Tyr Tyr Gly Val Pro Val Trp Lys
1               5                   10                  15
Glu Ala Thr Thr Thr Leu Phe Cys Ala Ser Asp Ala Lys Ala Tyr Asp
            20                  25                  30
Thr Glu Val His Asn Val Trp Ala Thr His Ala Cys Val Pro Thr Asp
        35                  40                  45
Pro Asn Pro Gln Glu Val Val Leu Glu Asn Val Thr Glu Asn Phe Asn
    50                  55                  60
Met Trp Lys Asn Asn Met Val Glu Gln Met His Glu Asp Ile Ile Ser
65                  70                  75                  80
Leu Trp Asp Gln Ser Leu Lys Pro Cys Val Lys Leu Thr Pro Leu Cys
                85                  90                  95
Val Thr Leu Asn Cys Thr Asp Asp Val Arg Asn Val Thr Asn Asn Ala
            100                 105                 110
Thr Asn Thr Asn Ser Ser Trp Gly Glu Pro Met Glu Lys Gly Glu Ile
        115                 120                 125
Lys Asn Cys Ser Phe Asn Ile Thr Thr Ser Ile Arg Asn Lys Val Gln
    130                 135                 140
Lys Gln Tyr Ala Leu Phe Tyr Lys Leu Asp Val Val Pro Ile Asp Asn
145                 150                 155                 160
Asp Ser Asn Asn Thr Asn Tyr Arg Leu Ile Ser Cys Asn Thr Ser Val
                165                 170                 175
```

```
Ile Thr Gln Ala Cys Pro Lys Val Ser Phe Glu Pro Ile Pro Ile His
            180                 185                 190

Tyr Cys Ala Pro Ala Gly Phe Ala Ile Leu Lys Cys Asn Asp Lys Lys
            195                 200                 205

Phe Asn Gly Thr Gly Pro Cys Thr Asn Val Ser Thr Val Gln Cys Thr
            210                 215                 220

His Gly Ile Arg Pro Val Val Ser Thr Gln Leu Leu Leu Asn Gly Ser
225                 230                 235                 240

Leu Ala Glu Glu Glu Val Val Ile Arg Ser Glu Asn Phe Thr Asn Asn
                245                 250                 255

Ala Lys Thr Ile Met Val Gln Leu Asn Val Ser Val Glu Ile Asn Cys
            260                 265                 270

Thr Arg Pro Asn Asn Asn Thr Arg Lys Ser Ile His Ile Gly Pro Gly
            275                 280                 285

Arg Ala Phe Tyr Thr Ala Gly Asp Ile Ile Gly Asp Ile Arg Gln Ala
            290                 295                 300

His Cys Asn Ile Ser Arg Ala Asn Trp Asn Asn Thr Leu Arg Gln Ile
305                 310                 315                 320

Val Glu Lys Leu Gly Lys Gln Phe Gly Asn Asn Lys Thr Ile Val Phe
                325                 330                 335

Asn His Ser Ser Gly Gly Asp Pro Glu Ile Val Met His Ser Phe Asn
            340                 345                 350

Cys Gly Gly Glu Phe Phe Tyr Cys Asn Ser Thr Lys Leu Phe Asn Ser
            355                 360                 365

Thr Trp Thr Trp Asn Asn Ser Thr Trp Asn Asn Thr Lys Arg Ser Asn
            370                 375                 380

Asp Thr Glu Glu His Ile Thr Leu Pro Cys Arg Ile Lys Gln Ile Ile
385                 390                 395                 400

Asn Met Trp Gln Glu Val Gly Lys Ala Met Tyr Ala Pro Pro Ile Arg
                405                 410                 415

Gly Gln Ile Arg Cys Ser Ser Asn Ile Thr Gly Leu Leu Leu Thr Arg
            420                 425                 430

Asp Gly Gly Asn Asp Thr Ser Gly Thr Glu Ile Phe Arg Pro Gly Gly
            435                 440                 445

Gly Asp Met Arg Asp Asn Trp Arg Ser Glu Leu Tyr Lys Tyr Lys Val
450                 455                 460

Val Lys Ile Glu Pro Leu Gly Val Ala Pro Thr Lys Ala Lys Glu Arg
465                 470                 475                 480

Val Val Gln Arg Glu Glu Arg Ala Val Gly Ile Gly Ala Val Phe Leu
                485                 490                 495

Gly Phe Leu Gly Ala Ala Gly Ser Thr Met Gly Ala Ala Ser Met Thr
            500                 505                 510

Leu Thr Val Gln Ala Arg Leu Leu Leu Ser Gly Ile Val Gln Gln Gln
            515                 520                 525

Asn Asn Leu Leu Arg Ala Ile Glu Ala Gln Gln His Leu Leu Gln Leu
530                 535                 540

Thr Val Trp Gly Ile Lys Gln Leu Gln Ala Arg Val Leu Ala Val Glu
545                 550                 555                 560

Arg Tyr Leu Lys Asp Gln Gln Leu Leu Gly Ile Trp Gly Cys Ser Gly
                565                 570                 575

Lys Leu Ile Cys Thr Thr Thr Val Pro Trp Asn Ala Ser Trp Ser Asn
            580                 585                 590

Lys Ser Leu Asp Lys Ile Trp Asn Asn Met Thr Trp Met Glu Trp Glu
```

-continued 595 600 605

Arg Glu Ile Asn Asn Tyr Thr Ser Leu Ile Tyr Thr Leu Ile Glu Glu
610 615 620

Ser Gln Asn Gln Gln Glu Lys Asn Glu Gln Glu Leu Leu Glu Leu Asp
625 630 635 640

Lys Trp Ala Ser Leu Trp Asn Trp Phe Asp Ile Ser Asn Trp Leu Trp
645 650 655

Tyr Ile Lys Ser Arg Ile Glu Gly Arg Gly Ser Gly Gly Tyr Ile Pro
660 665 670

Glu Ala Pro Arg Asp Gly Gln Ala Tyr Val Arg Lys Asp Gly Glu Trp
675 680 685

Val Leu Leu Ser Thr Phe Leu
690 695

<210> SEQ ID NO 3
<211> LENGTH: 29
<212> TYPE: PRT
<213> ORGANISM: Artificial Sequence
<220> FEATURE:
<223> OTHER INFORMATION: HIV leader/signal sequence

<400> SEQUENCE: 3

Met Arg Val Arg Gly Ile Gln Arg Asn Cys Gln His Leu Trp Arg Trp
1 5 10 15

Gly Thr Leu Ile Leu Gly Met Leu Met Ile Cys Ser Ala
20 25